United States Patent
Beine et al.

(10) Patent No.: US 8,172,110 B2
(45) Date of Patent: May 8, 2012

(54) CONTAINER FOR INFUSION LIQUIDS

(75) Inventors: Joachim Beine, Guxhagen (DE);
Torsten Dönhoff, Kassel (DE); Volker Harms, Kassel (DE); Hans-Otto Maier, Melsungen (DE)

(73) Assignee: B. Braun Melsungen AG, Melsungen (DE)

( * ) Notice: Subject to any disclaimer, the term of this patent is extended or adjusted under 35 U.S.C. 154(b) by 1240 days.

(21) Appl. No.: 10/571,985

(22) PCT Filed: Sep. 10, 2004

(86) PCT No.: PCT/EP2004/010125
§ 371 (c)(1),
(2), (4) Date: Jan. 5, 2007

(87) PCT Pub. No.: WO2005/032450
PCT Pub. Date: Apr. 14, 2005

(65) Prior Publication Data
US 2007/0272705 A1    Nov. 29, 2007

(30) Foreign Application Priority Data

Sep. 16, 2003  (DE) .................................. 103 42 742

(51) Int. Cl.
*B65D 35/56*    (2006.01)
*B65D 30/10*    (2006.01)
*A61B 19/00*    (2006.01)

(52) U.S. Cl. ........ 222/105; 222/107; 383/120; 383/124; 604/408; 604/415

(58) Field of Classification Search ................... 222/105, 222/107, 215, 181.1, 92, 93, 94, 95, 96, 97, 222/98, 99, 100, 101, 102, 103, 104, 106, 222/1; 215/11.3, 900, 12.1, 12.2; 220/6, 220/666, 62.2, 62.12, 62.13, 62.11; 604/408, 604/403, 409, 410, 416, 415; 383/120, 121, 383/104, 124; 264/254, 454; 322/257, 262, 322/279; 4/617; 128/DIG. 24
See application file for complete search history.

(56) References Cited

U.S. PATENT DOCUMENTS 1,733,219 A * 10/1929 Duvall ............................ 383/21
3,143,277 A * 8/1964 La Fleur ....................... 383/119

(Continued)

FOREIGN PATENT DOCUMENTS

DE     2719614     12/1977

(Continued)

OTHER PUBLICATIONS

Partial International Search Report completed Jan. 24, 2006, for PCT.EP2004/010125, mailed Feb. 2, 2005, 3 pgs.

*Primary Examiner* — Kevin P Shaver
*Assistant Examiner* — Stephanie E Williams
(74) *Attorney, Agent, or Firm* — Klein, O'Neill & Singh, LLP

(57) ABSTRACT

Containers for infusion liquids and methods for making the same are described herein. Aspects of an exemplary container include an extended hollow body, a standing bottom, collapsible side walls and a tapered shoulder region which transforms into a neck. Fold lines (BL) are provided and configured such that they cause portions of the container having the fold lines to be flattened when liquid is removed from the container without venting.

23 Claims, 3 Drawing Sheets

U.S. PATENT DOCUMENTS

| | | | | |
|---|---|---|---|---|
| 3,171,412 A | * | 3/1965 | Braun | 604/244 |
| 3,595,441 A | * | 7/1971 | Grosjean | 222/107 |
| 3,727,803 A | * | 4/1973 | Cobb | 222/215 |
| 3,926,341 A | | 12/1975 | Lhoest | |
| 4,547,900 A | * | 10/1985 | Larkin et al. | 383/5 |
| 4,674,655 A | * | 6/1987 | Lofgrer et al. | 222/48 |
| 4,986,053 A | * | 1/1991 | Schaefer | 53/401 |
| 5,174,458 A | * | 12/1992 | Segati | 215/383 |
| 5,255,808 A | | 10/1993 | Tobler | |
| 5,611,461 A | * | 3/1997 | Kubota et al. | 222/105 |
| 6,126,315 A | * | 10/2000 | Ichikawa et al. | 383/43 |
| 6,158,620 A | * | 12/2000 | Polan | 222/92 |
| 6,170,712 B1 | * | 1/2001 | Kasboske | 222/215 |
| 6,608,983 B2 | * | 8/2003 | Terazawa et al. | 399/258 |
| 7,005,150 B2 | * | 2/2006 | Kuge et al. | 426/85 |
| 7,156,556 B2 | * | 1/2007 | Takahashi et al. | 383/104 |
| 7,221,891 B2 | * | 5/2007 | Matsumoto et al. | 399/262 |
| 2004/0013325 A1 | * | 1/2004 | Cook | 383/104 |

FOREIGN PATENT DOCUMENTS

GB  2139551  11/1984

* cited by examiner

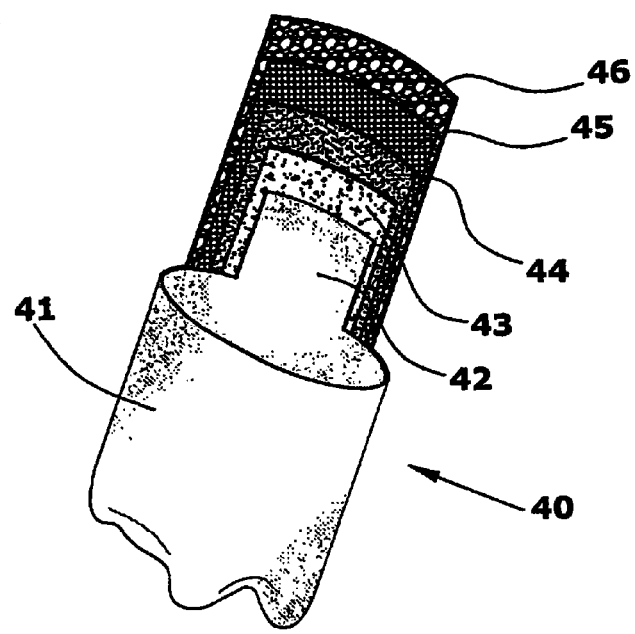
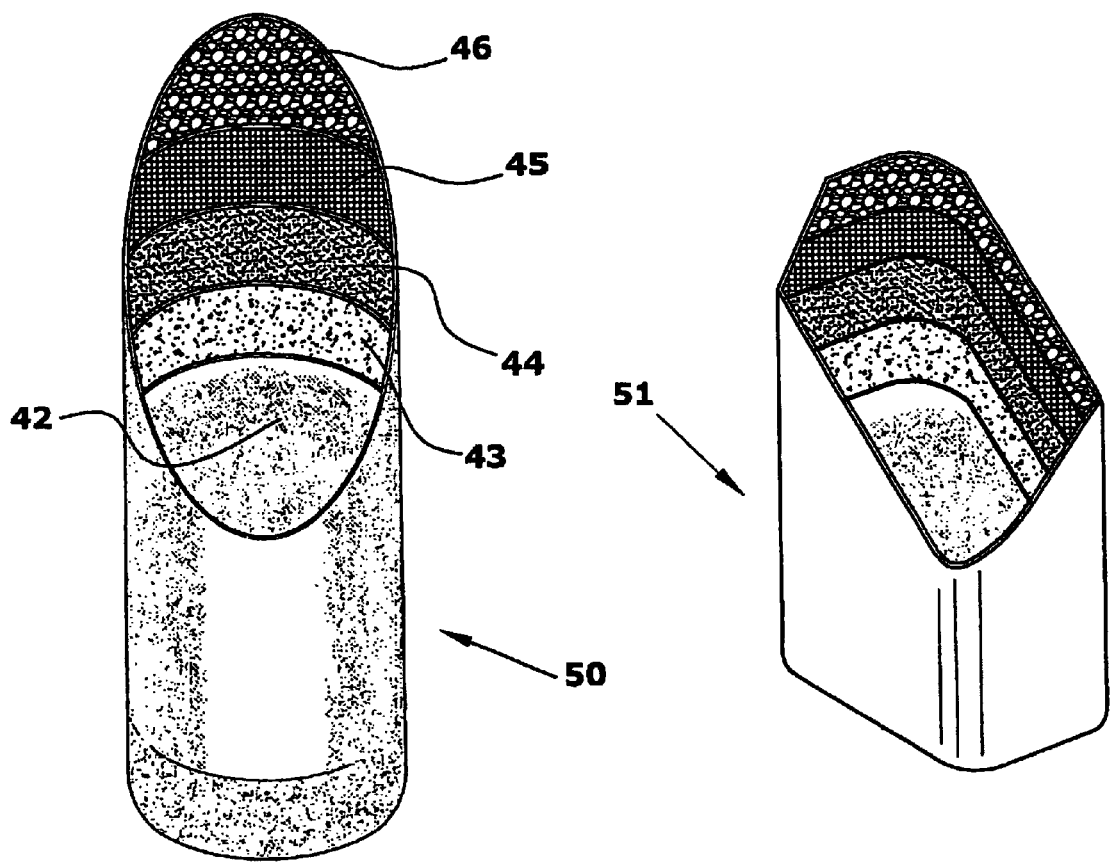
Fig.4
Fig.5  Fig.6

CONTAINER FOR INFUSION LIQUIDS

CROSS-REFERENCE TO RELATED APPLICATIONS

This application claims priority to International Application No. PCT/EP2004/010125, filed Sep. 16, 2003, entitled A CONTAINER FOR INFUSION LIQUIDS, its contents are expressly incorporated herein by reference.

FIELD OF THE INVENTION

The invention refers to a molded container for infusion liquids, adapted to stand and comprising walls forming a standing bottom and a shoulder portion merging into a neck portion.

BACKGROUND

Glass containers are known that contain an infusion liquid which is fed to a patient through a hose system. Such containers are closed with a rubber-resilient stopper pierceable by the spike of a transfer device. The container is then suspended with its opening directed downward so that the liquid can flow out in a controlled manner through the withdrawing device. Air is allowed into the container through a venting channel of the penetrating spike so as to fill the volume cleared by the liquid and to avoid a vacuum in the container.

Such rigid containers are not suited for pressurized infusions where the infusion liquid is pressed from the container by applying external pressure. Pressurized infusions are applied to patients in a hypervolemic condition after loss of larger amounts of blood, e.g. after a traffic accident, in order to supply a large volume of liquid to the patient in a short span of time. Foil bags containing the infusion liquid are suited for such pressurized infusions. The foil bags contain no air and their volume adapts to the respective volume of the liquid. However, the manufacture of suitable foil bags is rather troublesome. As the material, multi-layered composite foils are used with at least one of the layers having special barrier properties.

More economic to manufacture are molded containers made and filled according to the blow-fill-seal method (BFS), wherein all process steps—blow molding the container, filling it and sealing it hermetically—occur in the molding tool.

Further known is a container of oval shape distributed by B. Braun Melsungen AG under the trade name Ecoflac plus® which is made in a BFS process and whose wall contracts when an infusion without additional venting is applied. However, the standing bottom and the shoulder portion of this container remain undeformed because of the stability imparted by the molding so that only the middle portion is constricted. This means that cavities will remain in the standing bottom and the shoulder portion even with the container collapsed. These cavities have to be filled with air to allow for a typical gravity infusion to be carried with this container. Such a gravity infusion requires that a volume of air is always present in the container. The required volume of air is rather large because of the dimensional stability of the end portions of the container mentioned. On the other hand, air has to be prevented from entering into the hose system of the transfer device since this would cause a risk of air embolism to the patient.

JP 2002 282 335 A describes an infusion container corresponding to the preamble of claim 1. The infusion container comprises a molded body that can be folded in an empty state prior to filling and after the withdrawal of the liquid. During the filling of the infusion liquid and during shipping after the filling, however, the container can stand upright. On two opposite side faces, the container has respective outer fold lines in the shape of an inverted Y and a transverse inner fold line connecting the outer fold lines. When folding the container bottom up, the outer fold lines deflect outward, whereas the inner fold line buckles. No folding occurs in the neck portion of the container. The container is deformed by manual action, the deforming behavior being influenced by the point at which the pressure is applied.

DE 37 27 972 A1 describes a liquid container in the form of a bag for receiving beverages such as orange juice and soft drinks. The bag is a side gusseted bag with a plurality of vertical welds. The bottom is made from flaps folded over each other. The bag can only stand unsupported when it is filled. It is not intended for suspending.

DE 699 03 510 T2 describes a generally cubic large bag for use in the biopharmaceutic industry which is designed as a bellows bag of welded foils. It is not a molded container. Further, the container neither has a neck portion nor a shoulder portion.

A side gusseted bag for medical purposes is described in DE 699 00 761 T2. The side gusseted bag is parallelepiped in shape when filled, the bottom being made of triangular flaps connected by sealing seams. Foil bags with numerous sealing seams require rather complex manufacturing.

DE 43 15 966 describes a foldable container made of an integral molded part and having longitudinal side gussets. The container is intended for manual compression so as to require less volume when it is disposed as waste.

SUMMARY OF THE PREFERRED EMBODIMENTS

It is the object of the present invention to provide a molded container that is easy and economically to manufacture and allows for pressurized infusions without requiring a larger volume of air.

The molded standing container of the present invention has the features of claim 1.

According thereto, the fold lines are arranged and configured such that they cause the portion having the fold lines to be flattened when liquid is removed from the container without venting.

As used herein, a "molded container" is a container whose shape is determined upon manufacture and which therefore has a predetermined shape which, in contrast to a foil bag, it retains when set on a support. This ability to stand may be influenced positively by nubs formed thereon. However, the present container is deformable by exterior air pressure (ambient pressure) when a volume is removed from the from within the container. Further, the container can be deformed by exerting force on the container wall in order to make a pressurized infusion.

Due to the fact that not only the middle portion of the molded container deforms when liquid is removed therefrom, but also the end portions formed by the standing bottom and the shoulder portion, the volume of air required for allowing the container to empty is reduced substantially. Thus, it is necessary only to provide a minimum volume of air corresponding to this residual volume. When filled, the container is almost free of air. This means that the volume of air makes up 15% of the container volume at most. With the known molded containers, the volume of air is 20-40% of the container volume, depending on the filling volume/container size. Since the present container is still partly impressed when in the filled state, thus still having a reserve volume for adding a supplementary injection, a larger volume of air is not required.

In the event of a withdrawal of the contents without venting, the molded container will run empty uniformly despite the lacking volume of air. Therefore, it has a good measurability.

The container of the present invention can be manufactured with relative ease, e.g. by a BSF process, either with a single layer or with multiple layers. The advantages of a foil bag, namely a minimum residual volume or volume of air, and of a container made by a BSF process, namely an economic production, are combined in the present container.

In a preferred embodiment of the invention, the fold lines are formed in the walls by an intentional manipulation of the course of the wall thickness. Such a fold line can be molded in the blow molding process. To this avail, the blow mold must be equipped with corresponding ribs causing an image of the fold lines mentioned above.

The foldability of the shoulder portion is achieved preferably by arranging a plurality of fold lines in a group such that they form an accordion-like folding. The dimensional stability of the shoulder portion is usually high since the shoulder portion is pyramidal or truncated, depending on the container geometry. The dimensional stability is increased further by the shoulder portion being delimited by body edges of increased flexural stiffness. The relatively large volume included by the shoulder portion is reduced substantially by the accordion-like folding and the corresponding flattening.

In the standing bottom, a fold line can be formed as a transverse fold which wanders outward during flattening. The standing bottom should generally be designed such that it moves outward (not inward) upon flattening, since the container volume can be reduced most in this manner.

The invention further refers to a method for filling a container with infusion liquid after molding. If a liquid, e.g. a medicament, is added by injection into an infusion container, the closed container has to receive an additional volume of liquid. With a rigid container, this will increase the internal pressure in the container. In the case of a flexible bag, the bag wall is stretched further.

It is the object of the novel method to provide a method for filling a container with which it can be guaranteed that no substantial mechanic stress of the container occurs when a liquid is added by injection.

According to claim 8, this is achieved by compressing the container after molding, so as to reduce its volume, and by filling it in this state, wherein the compression provides for a backup volume for receiving a supplementary volume injected later. Compressing the container means that not the entire volume of the container is available in the filling operation. Rather, a part of a wall is forcibly deformed such that the wall does not assume the substantially relaxed final state, but bulges inward. Thus, the container is filled only incompletely, to be able to afterwards receive a supplementary amount injected, whereby it reaches its specified final volume.

The following is a detailed description of an embodiment of the invention with reference to the drawings. The following description should not be construed as being limitative to the scope of the patent. Rather, the same is defined by the claims.

DETAILED DESCRIPTION

Figure 1:
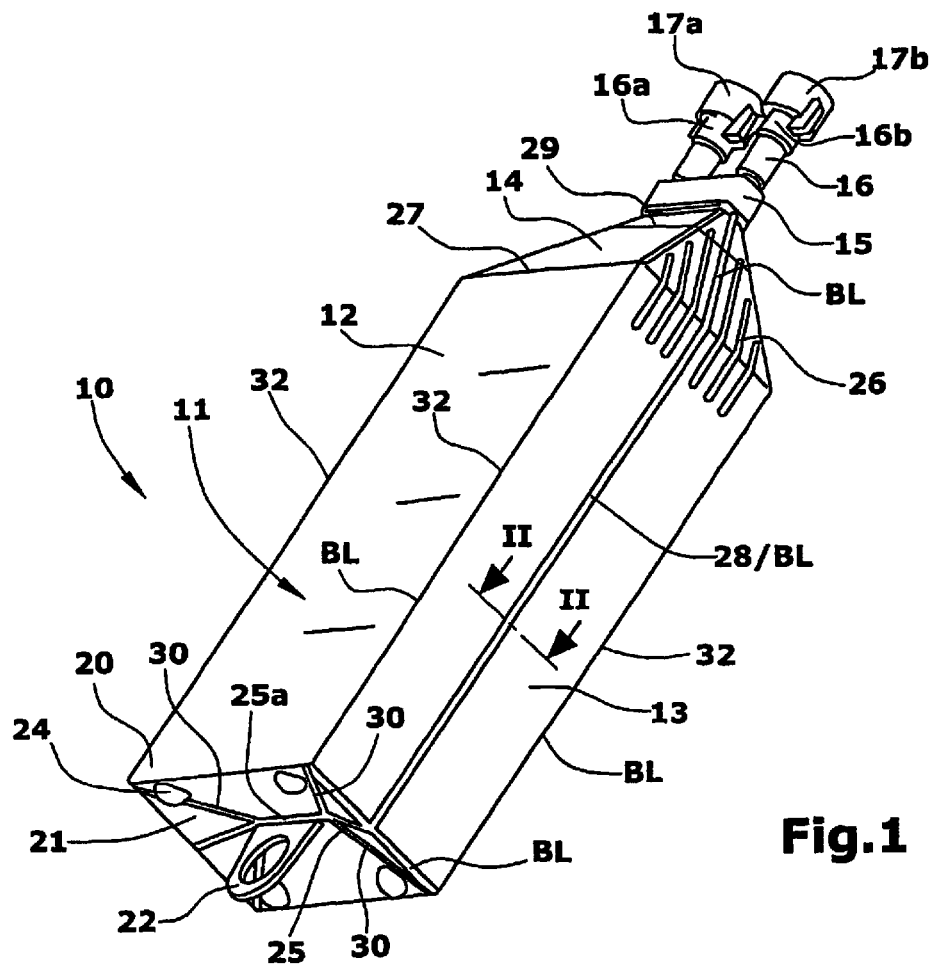
FIG. 1 is a perspective view or a dimensionally stable container of the present invention.

The container 10 illustrated has an elongate hollow body 11, delimited by four walls 12, 13. The body 11 is rectangular in shape. At one end, it passes into a shoulder portion 14 in the form of a frustum of pyramid, which is adjoined by an elongate rectangular neck portion 15 extending in parallel with the walls 12. A port system 16 having two ports 16a, 16b sits on the neck portion 15, each port being provided with a withdrawal opening including a pierceable membrane. Each port has a tear-off member 17a, 17b that can be torn off to expose the membrane so that the spike of a transfer device can penetrate the same. One of the ports serves as a withdrawal port and the other as a port for supplementary injection. Projecting tabs are provided on the sides of the ports, thereby allowing for the connection of monovial containers.

The standing bottom 20 of the body 11 includes a bottom wall 21. A suspension tab 22 protrudes therefrom so as to allow the container to be suspended with the withdrawal opening directed downward. In addition, the standing bottom may comprise standing knobs 24 for a better handling of the container. The standing knobs 24 provide a free space for storing the laterally deflected suspension tab and cause a secure and non-tilting stand of the container.

Except for the port system 16, the container 10 is made integrally and filled with infusion liquid. Typically, it is made from materials of polyolefinic nature, e.g. LDPE, LLDPE. PP.

To provide for the deformability necessary for pressurized infusion, the container has fold lines BL extending mainly in the standing bottom 20 and in the shoulder region 14. One fold line 25a extends across the standing bottom 20. The fold line 25a has a middle portion from which the tab 22 protrudes. Further fold lines 30 branch from the two ends of the middle portion, radiating to the corners of the bottom wall 21. A group of fold lines 26 arranged like a rake extends in the shoulder portion 14 and from there into the body 11. The fold lines 26 generally extend in the longitudinal direction of the container and they are arranged such that they form an accordion-like folding, the transition edge 27 between the body 11 and the shoulder portion 14 being broken.

One or also a plurality of further fold lines 28 extend along a wall 13 in the longitudinal direction of the container. Further fold lines 32 are provided at the longitudinally extending edges of the container. Whereas the fold line 28 forms an inner fold, the fold lines 32 form outer folds connecting the corners of the body 11. One or also a plurality of corresponding fold lines extend on the opposite wall not visible in FIG. 1. Upon flattening the container, the fold lines 28 move inward and the fold line 25 in the bottom wanders outward.

Figure 2:
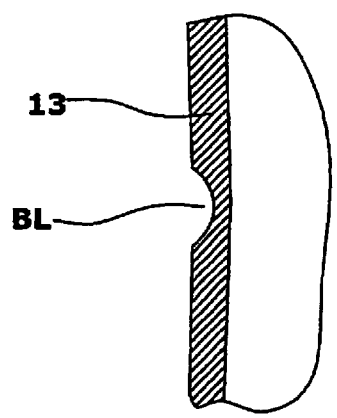
FIG. 2 is a cross section through a fold line along the line II-II of FIG. 1.

FIG. 2 is a cross section of the wall 13 with the fold line BL formed therein. The wall thickness is reduced along the fold line so that the flexural stiffness is substantially reduced there. When the container is made by blow molding, the fold line BL can be made by providing the wall of the blow mold with a rib facing the mold cavity. This forms the fold line on the exterior of the container, whereas the inner surface of the container is smooth. Generally, the fold can also be made on the inner surface of the container by recesses in the tool.

The container described is filled completely or almost completely with liquid. In the embodiment described, the liquid level 29 is in the upper part of the shoulder portion 14 when the container is standing upright. Above that is only a small volume of air that is sufficient to fill the container volume still remaining in the deformed container.

Figure 3:
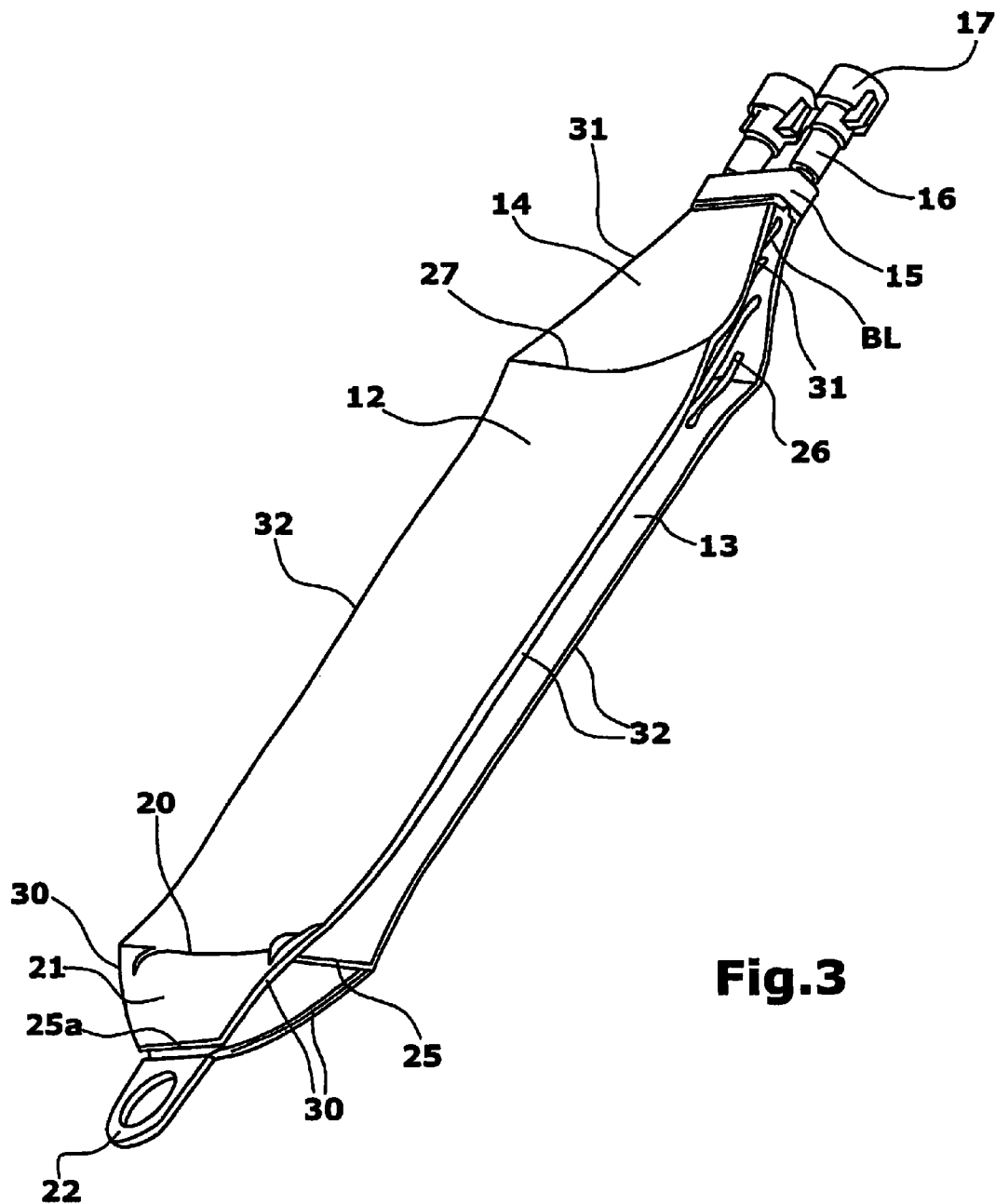
FIG. 3 is a perspective illustration of the container after withdrawal of the contents, FIG. 4 a multi-layered container of the present invention, cut open to illustrate the layered structure, FIG. 5 a preform for producing a multi-layered container by (co)extrusion blow molding, the preform having a circular cross section, and FIG. 6 an embodiment of a preform for a multi-layered container, the perform having an elongate cross section with parallel side walls and rounded end walls.

FIG. 3 illustrates the container in the collapsed state after withdrawal of the contents. As can be seen, the side walls 13 are folded longitudinally like the walls of a side gusseted bag and have their halves laid against each other, the fold line 28 forming an inner fold and the fold lines 32 form outer folds. This lateral folding continues into the standing bottom 20 and the shoulder portion 14. The shoulder portion 14 also has fold lines forming a continuation of the longitudinal fold lines 28 and 32 of the body 11.

FIG. 4 illustrates a container 40 in a cut open state, the container having a cylindrical container wall 41 which may be made of a single layer or multiple layers. The number of layers is between 1 and 10. In the embodiment illustrated, the following layers exist:

an inner layer 42 of polypropylene (PP), preferably polypropylene copolymer (CoPP), a layer of adhesive agent 43 of modified polyolefin with functional anhydride groups, at least one barrier layer 44 of polyamide (PA), preferably polyamide copolymer (CoPA) and/or ethylene/vinyl alcohol copolymer (EVOH), an outer layer of adhesive agent 45 of a structure similar to that of the inner layer of adhesive agent 43, an outer layer 46 of polyamide (PA), preferably polyamide copolymer (CoPA) and/or polyester (PET), preferably copolyester (CoPET).

The total wall thickness of the container wall 41 is between 0.1 mm and 0.7 mm. About 40% to 70% of the total wall thickness are made up by the inner layer 42 and 10% by barrier layer 44 and the layers 43 and 45 of adhesive agent. The rest of the wall thickness is made up by the outer layer 46.

For the manufacture of the container of FIG. 4, first the multi-layered preform of FIG. 5 is made by (co)extrusion. The preform 50 is a straight tube of circular cross section in the present case, comprising the individual layers 42 to 46 in a coaxial tubular arrangement. The preform is expanded in a blow mold and given its final shape. In doing so, the wall thickness is reduced to between 0.1 mm and 0.7 mm. The materials used are selected such that the container has a high transparency in combination with the reduced wall thickness, which clearly differs from the transparency of typical (co) extruded blow molded container for infusion solutions of a polyolefinic structure (PP/PE/COC). In addition to the material properties, a significant increase in transparency can be achieved by axially stretching the preform prior to the blow molding.

FIG. 6 illustrates another preform 51 with a profiled cross section differing from the round cross section. The cross section of the preform 51 which has the same layers as the preform 50 is one of an elongate rectangle with heavily rounded corners. The extrusion die (not illustrated) in the tool head of the extruder has a corresponding profile shape. The distribution of material in the preform 51 is selected such that a circumferentially uniform wall thickness of the container is obtained by the subsequent expansion in the blow molding operation.

The container illustrated in FIG. 4 is preferably molded such that this container has fold lines in the walls of the standing bottom and/or the shoulder portion. Given the reduced wall thickness mentioned above, it is also possible that the container deforms in the region of the standing bottom and in the shoulder portion upon withdrawal of liquid from the container, without such fold lines being provided. However, preformed fold lines or weakened portions facilitate a defined collapsing and an orderly folding of the container.

The invention claimed is:

1. A molded container for liquid infusion, said container comprising:
   a plurality of walls including a first side wall and a second side wall, two collapsible walls each disposed in between the first side wall and the second side wall each comprising a longitudinal fold line, a bottom wall comprising a perimeter having at least four perimeter edges configured for standing upright, and a shoulder portion having a port for filling fluid into or discharging fluid out of an interior cavity defined by the plurality of walls;
   wherein the bottom wall comprises an interior wall surface, an exterior wall surface, a lateral fold line intersecting each longitudinal fold line along two of the perimeter edges to define two intersecting fold points and separating the interior wall surface into a first interior section and a second interior section, and at least two transverse fold lines that are angled to one another; and
   wherein portions of the first interior section and the second interior section of the bottom wall move closer to one another and wherein portions of the exterior wall surface of the bottom wall move outwardly away from the interior cavity from a first position relative to the interior cavity to a second further outward position relative to the interior cavity when the container collapses.

2. The container of claim 1, wherein the lateral fold line is formed by a weakened portion in the bottom wall.

3. The container of claim 2, wherein the two collapsible walls each comprises two or more longitudinal fold lines.

4. The container of claim 3, wherein the longitudinal fold lines are arranged in a group such that they form an accordion-like folding.

5. The container of claim 1, wherein the transverse fold lines move outward during flattening.

6. The container of claim 1, wherein the two intersecting fold points are movable between extended positions when the container is filled and retracted positions inwardly of the extended positions when the container collapses.

7. The container of one of claim 1, wherein when the container is filled, the container contains a volume of air of at most 15% of the container volume.

8. The container of claim 1, wherein the filling volume of the container is 1 ml to 5000 ml.

9. The container of claim 1, wherein the port comprises a pierceable membrane.

10. The container of claim 1, wherein the bottom wall comprises a projecting suspension lug.

11. A method for manufacturing a molded standing container for infusion liquids comprising the steps:
    extruding a preform of a polymer material; and
    expanding the preform by blow molding to form the container, the container comprising a plurality of side walls and a bottom wall defining an interior cavity; at least two of the side walls each comprising a longitudinal fold line;
    wherein the bottom wall comprises a fold line and a rectangular perimeter attached to the plurality of side walls and wherein the fold line comprises a weakened portion and intersecting the two longitudinal fold lines along a first side and a second side of the perimeter to define two intersecting fold points; and wherein the bottom wall is configured to fold at the fold line when the container collapses and the fold line moves outwardly away from the interior cavity from a first position relative to the interior cavity to a second further outward position relative to the interior cavity.

12. The method of claim 11, wherein the plurality of walls are made with a wall thickness of about 0.1 mm to about 0.7 mm.

13. The method of claim 11, wherein the container is transparent and the transparency is increased by axially stretching the preform.

14. The method of claim 11, wherein the preform is a multi-layer preform comprising an overall wall thickness.

15. The method of claim 14, wherein at least one of the layers is a layer of adhesive agent.

16. The method of claim 14, wherein at least one of the layers is made from a polyamide or an ethylene/vinyl alcohol material.

17. The method of claim 14, wherein the two intersecting fold points are configured to move from extended positions relative to the interior cavity to retracted positions inwardly of the extended positions when the container collapses.

18. The method of claim 14, wherein 40% to 70% of the overall wall thickness is made up by an inner layer, 10% by a barrier layer and at least one layer of adhesive agent, and an outer layer of remaining balance of thickness.

19. A method for filling a container of claim 1 with infusion liquid, characterized in that the container is impressed after molding to reduce its volume and is filled and closed in this state, the impressing providing for a backup volume for receiving a supplementary volume injected later.

20. A molded container for liquid infusion, said container comprising:
   a plurality of side walls and a bottom wall defining an interior cavity and a shoulder portion of reduced cross-section forming a discharge end, the bottom wall comprising a perimeter having at least four perimeter edges, an exterior surface and an interior surface;
   said plurality of side walls comprising a longitudinal fold line on at least two of the side walls for collapsing the container;
   said bottom wall comprising a plurality of fold lines with at least two of the fold lines angled to one another including one lateral fold line that intersects the two longitudinal fold lines along two of the perimeter edges to define two intersecting fold points;
   wherein when the container collapses, the two intersecting fold points are configured to move inwardly from extended positions to retracted positions and portions of the exterior surface move outwardly away from the interior cavity from a first position relative to the interior cavity to a second further outward position; and
   wherein the bottom wall is folded along the plurality of fold lines.

21. The container of claim 20, wherein the plurality of side walls are integrally formed.

22. The container of claim 20, wherein the plurality of side walls are made from a multi-layer preform.

23. The container of claim 20, wherein the discharge end comprises two ports.

* * * * *

UNITED STATES PATENT AND TRADEMARK OFFICE
CERTIFICATE OF CORRECTION

| | | |
|---|---|---|
| PATENT NO. | : 8,172,110 B2 | Page 1 of 1 |
| APPLICATION NO. | : 10/571985 | |
| DATED | : May 8, 2012 | |
| INVENTOR(S) | : Joachim Beine et al. | |

It is certified that error appears in the above-identified patent and that said Letters Patent is hereby corrected as shown below:

On the Title page, in Item (56), under "Other Publications", in column 2, line 2, delete "PCT.EP2004/010125," and insert -- PCT/EP2004/010125, --, therefor.

In column 1, line 7, delete "Sep. 16, 2003," and insert -- Sep. 10, 2004, --, therefor.

In column 2, line 49, after "removed" delete "from the".

In column 4, line 1, before "a" insert -- is --.

In column 4, line 3, before "a" insert -- is --.

In column 4, line 6, before "an" insert -- is --.

In column 4, line 7, delete "perform" and insert -- preform --, therefor.

Signed and Sealed this
Eleventh Day of December, 2012

David J. Kappos
*Director of the United States Patent and Trademark Office*